US012758252B2

(12) United States Patent
Sowards et al.

(10) Patent No.: US 12,758,252 B2
(45) Date of Patent: Oct. 13, 2026

(54) SYSTEMS AND METHODS FOR AUTOMATIC DETERMINATION OF NEEDLE GUIDES FOR VASCULAR ACCESS

(71) Applicant: Bard Access Systems, Inc., Salt Lake City, UT (US)

(72) Inventors: Steffan Sowards, Salt Lake City, UT (US); Anthony K. Misener, Bountiful, UT (US); William Robert McLaughlin, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 175 days.

(21) Appl. No.: 17/859,980

(22) Filed: Jul. 7, 2022

(65) Prior Publication Data

US 2024/0008894 A1 Jan. 11, 2024

(51) Int. Cl.
*A61B 17/34* (2006.01)
*A61B 8/00* (2006.01)
(Continued)

(52) U.S. Cl.
CPC .......... *A61B 17/3403* (2013.01); *A61B 8/085* (2013.01); *A61B 8/0891* (2013.01);
(Continued)

(58) Field of Classification Search
None
See application file for complete search history.

(56) References Cited

U.S. PATENT DOCUMENTS 5,325,293 A 6/1994 Dorne
5,549,554 A 8/1996 Miraki
(Continued)

FOREIGN PATENT DOCUMENTS

CN 101854853 A 10/2010
CN 105054962 A * 11/2015
(Continued)

OTHER PUBLICATIONS

CN-105054962-A—translation, translated through patent translate on Jun. 26, 2024 (Year: 2015).*
(Continued)

*Primary Examiner* — Christopher Koharski
*Assistant Examiner* — Renee C Langhals
(74) *Attorney, Agent, or Firm* — Rutan & Tucker LLP

(57) ABSTRACT

Disclosed are systems and methods for automatically determining needle guides for establishing vascular access. For example, a system can include an ultrasound probe, a console operably coupled to the ultrasound probe, and a display screen integrated into the console. The console can include one or more processors and memory including instructions configured to instantiate one or more processes when executed by the one-or-more processors for automatic determination of a needle guide in accordance with ultrasound-imaging data, historical data, or a combination thereof. The automatic determination of such a needle guide can use logic, algorithms, machine learning, artificial intelligence, or a combination thereof. The display screen can be configured to display an ultrasound image including one or more blood vessels below a skin surface of a patient as well as the needle guide resulting from the automatic determination for establishing vascular access to the one-or-more blood vessels in the ultrasound image.

21 Claims, 4 Drawing Sheets

(51) Int. Cl.
*A61B 8/08* (2006.01)
*G06N 20/00* (2019.01)
*G16H 30/20* (2018.01)

(52) U.S. Cl.
CPC .............. *A61B 8/463* (2013.01); *A61B 8/488* (2013.01); *G06N 20/00* (2019.01); *G16H 30/20* (2018.01); *A61B 2017/3405* (2013.01); *A61B 2017/3413* (2013.01)

(56) References Cited

U.S. PATENT DOCUMENTS

| | | | |
|---|---|---|---|
| 5,573,529 | A | 11/1996 | Haak et al. |
| 5,908,387 | A | 6/1999 | LeFree et al. |
| 5,970,119 | A | 10/1999 | Hofmann |
| 5,997,497 | A | 12/1999 | Nita et al. |
| 6,012,034 | A | 1/2000 | Hamparian et al. |
| 6,074,367 | A | 6/2000 | Hubbell |
| 6,543,642 | B1 | 4/2003 | Milliorn |
| 6,554,771 | B1 | 4/2003 | Buil et al. |
| 6,592,565 | B2 | 7/2003 | Twardowski |
| 6,601,705 | B2 | 8/2003 | Molina et al. |
| 6,612,992 | B1 | 9/2003 | Hossack et al. |
| 6,613,002 | B1 | 9/2003 | Clark et al. |
| 6,687,386 | B1 | 2/2004 | Ito et al. |
| 6,702,749 | B2 | 3/2004 | Paladini et al. |
| 6,754,608 | B2 | 6/2004 | Svanerudh et al. |
| 6,840,379 | B2 | 1/2005 | Franks-Farah et al. |
| 6,857,196 | B2 | 2/2005 | Dalrymple |
| 7,831,449 | B2 | 11/2010 | Ying et al. |
| 9,521,961 | B2 | 12/2016 | Silverstein et al. |
| 9,756,766 | B2 | 9/2017 | Best |
| 9,949,720 | B2 | 4/2018 | Southard et al. |
| 9,950,139 | B2 | 4/2018 | Blanchard et al. |
| 10,849,689 | B1 | 12/2020 | Hu et al. |
| 11,462,324 | B1 | 10/2022 | Roh et al. |
| 11,844,656 | B2 | 12/2023 | Urabe et al. |
| 11,896,425 | B2 | 2/2024 | Dhatt et al. |
| 11,974,813 | B1 | 5/2024 | Donhowe et al. |
| 2003/0028112 | A1 | 2/2003 | Paladini et al. |
| 2003/0047126 | A1 | 3/2003 | Tomaschko |
| 2003/0106825 | A1 | 6/2003 | Molina et al. |
| 2003/0120154 | A1 | 6/2003 | Sauer et al. |
| 2003/0120155 | A1 | 6/2003 | Sauer et al. |
| 2003/0199765 | A1 | 10/2003 | Stetten et al. |
| 2004/0055925 | A1 | 3/2004 | Franks-Farah et al. |
| 2005/0000975 | A1 | 1/2005 | Carco et al. |
| 2005/0165299 | A1 | 7/2005 | Kressy et al. |
| 2006/0004290 | A1 | 1/2006 | Smith et al. |
| 2006/0015039 | A1 | 1/2006 | Cassidy et al. |
| 2006/0020256 | A1 | 1/2006 | Bell et al. |
| 2007/0043341 | A1 | 2/2007 | Anderson et al. |
| 2007/0073155 | A1 | 3/2007 | Park et al. |
| 2007/0199848 | A1 | 8/2007 | Ellswood et al. |
| 2007/0239120 | A1 | 10/2007 | Brock et al. |
| 2007/0249911 | A1 | 10/2007 | Simon |
| 2007/0260213 | A1 | 11/2007 | Williams et al. |
| 2008/0009747 | A1 | 1/2008 | Saadat et al. |
| 2008/0033293 | A1 | 2/2008 | Beasley et al. |
| 2008/0033759 | A1 | 2/2008 | Finlay |
| 2008/0051657 | A1 | 2/2008 | Rold |
| 2008/0058963 | A1 | 3/2008 | Garibaldi et al. |
| 2008/0161687 | A1 | 7/2008 | Suri et al. |
| 2008/0177186 | A1 | 7/2008 | Slater et al. |
| 2008/0218743 | A1 | 9/2008 | Stetten et al. |
| 2008/0300491 | A1 | 12/2008 | Bonde et al. |
| 2009/0143672 | A1 | 6/2009 | Harms et al. |
| 2009/0143684 | A1 | 6/2009 | Cermak et al. |
| 2009/0156926 | A1 | 6/2009 | Messerly et al. |
| 2009/0182224 | A1 | 7/2009 | Shmarak et al. |
| 2009/0221908 | A1 | 9/2009 | Glossop |
| 2009/0234328 | A1 | 9/2009 | Cox et al. |
| 2009/0306509 | A1 | 12/2009 | Pedersen et al. |
| 2010/0080427 | A1 | 4/2010 | Yeluri et al. |
| 2010/0106015 | A1 | 4/2010 | Norris |
| 2010/0106056 | A1 | 4/2010 | Norris |
| 2010/0211026 | A2 | 8/2010 | Sheetz et al. |
| 2010/0305442 | A1 | 12/2010 | Tierney et al. |
| 2010/0312121 | A1 | 12/2010 | Guan |
| 2011/0028847 | A1* | 2/2011 | Whitmore, III ....... A61B 90/11 600/461 |
| 2011/0071404 | A1 | 3/2011 | Schmitt et al. |
| 2011/0166451 | A1 | 7/2011 | Blaivas et al. |
| 2011/0245659 | A1 | 10/2011 | Ma et al. |
| 2011/0295108 | A1 | 12/2011 | Cox et al. |
| 2011/0313293 | A1 | 12/2011 | Lindekugel et al. |
| 2012/0078103 | A1 | 3/2012 | Tashiro et al. |
| 2012/0143029 | A1 | 6/2012 | Silverstein et al. |
| 2012/0165679 | A1 | 6/2012 | Orome et al. |
| 2012/0197132 | A1 | 8/2012 | O'Connor |
| 2012/0253200 | A1 | 10/2012 | Stolka et al. |
| 2013/0006102 | A1 | 1/2013 | Wilkes et al. |
| 2013/0102889 | A1 | 4/2013 | Southard et al. |
| 2013/0131499 | A1 | 5/2013 | Chan et al. |
| 2013/0218024 | A1 | 8/2013 | Boctor et al. |
| 2013/0261553 | A1 | 10/2013 | Sheldon et al. |
| 2014/0155744 | A1 | 6/2014 | Pameijer |
| 2014/0275997 | A1 | 9/2014 | Chopra et al. |
| 2014/0287393 | A1 | 9/2014 | Kumar et al. |
| 2014/0303423 | A1 | 10/2014 | Amthor et al. |
| 2014/0343406 | A1 | 11/2014 | Damjanovic |
| 2015/0148668 | A1 | 5/2015 | Stolka et al. |
| 2015/0182144 | A1 | 7/2015 | Bharat et al. |
| 2015/0216442 | A1 | 8/2015 | Lavy et al. |
| 2015/0250437 | A1 | 9/2015 | Zaiki |
| 2015/0272553 | A1 | 10/2015 | Thattari Kandiyil et al. |
| 2015/0320325 | A1 | 11/2015 | Sheehan et al. |
| 2015/0320481 | A1 | 11/2015 | Cosman, Jr. et al. |
| 2015/0359991 | A1 | 12/2015 | Dunbar et al. |
| 2016/0051224 | A1 | 2/2016 | Striano |
| 2016/0128719 | A1 | 5/2016 | Cermak |
| 2016/0174937 | A1 | 6/2016 | Bakshi et al. |
| 2016/0213398 | A1 | 7/2016 | Liu |
| 2016/0300120 | A1 | 10/2016 | Haas et al. |
| 2016/0302772 | A1 | 10/2016 | Cummins et al. |
| 2016/0331469 | A1 | 11/2016 | Hall et al. |
| 2016/0374644 | A1 | 12/2016 | Mauldin, Jr. et al. |
| 2017/0035514 | A1* | 2/2017 | Fox ........................ G06Q 10/10 |
| 2017/0056062 | A1 | 3/2017 | Buljubasic |
| 2017/0079551 | A1 | 3/2017 | Henkel et al. |
| 2017/0188990 | A1 | 7/2017 | Von Allmen et al. |
| 2017/0245831 | A1 | 8/2017 | Nishigaki et al. |
| 2017/0265946 | A1 | 9/2017 | Ramachandran et al. |
| 2017/0290563 | A1 | 10/2017 | Cole et al. |
| 2018/0015256 | A1 | 1/2018 | Southard et al. |
| 2018/0036084 | A1 | 2/2018 | Krimsky |
| 2018/0061546 | A1 | 3/2018 | Ma et al. |
| 2018/0125450 | A1 | 5/2018 | Blackbourne et al. |
| 2018/0132944 | A1 | 5/2018 | Yan et al. |
| 2018/0228465 | A1 | 8/2018 | Southard et al. |
| 2018/0289929 | A1 | 10/2018 | Ma et al. |
| 2018/0310955 | A1 | 11/2018 | Lindekugel et al. |
| 2019/0000478 | A1 | 1/2019 | Messerly et al. |
| 2019/0026438 | A1 | 1/2019 | Ma et al. |
| 2019/0105017 | A1 | 4/2019 | Hastings |
| 2019/0282262 | A1 | 9/2019 | Bouazza-Marouf et al. |
| 2019/0298278 | A1 | 10/2019 | Nachabe et al. |
| 2019/0374290 | A1 | 12/2019 | Stolka et al. |
| 2020/0090331 | A1 | 3/2020 | Mansi et al. |
| 2020/0113540 | A1 | 4/2020 | Gijsbers et al. |
| 2020/0219258 | A1 | 7/2020 | Saget et al. |
| 2020/0230391 | A1 | 7/2020 | Burkholz et al. |
| 2020/0234812 | A1 | 7/2020 | Willybiro et al. |
| 2020/0237403 | A1 | 7/2020 | Southard et al. |
| 2020/0245969 | A1 | 8/2020 | Tung et al. |
| 2020/0275949 | A1 | 9/2020 | Masotti et al. |
| 2020/0297235 | A1 | 9/2020 | Sanchez et al. |
| 2020/0315592 | A1 | 10/2020 | Soleimani et al. |
| 2020/0359990 | A1 | 11/2020 | Poland et al. |
| 2020/0397399 | A1 | 12/2020 | Adams et al. |
| 2021/0015448 | A1 | 1/2021 | Sokulin et al. |
| 2021/0045717 | A1 | 2/2021 | Schwab |
| 2021/0059636 | A1 | 3/2021 | Durfee et al. |
| 2021/0085282 | A1 | 3/2021 | Prince |

(56) References Cited

U.S. PATENT DOCUMENTS

| | | | | |
|---|---|---|---|---|
| 2021/0138130 | A1 | 5/2021 | Kotanko et al. | |
| 2021/0169585 | A1 | 6/2021 | Prince et al. | |
| 2021/0186456 | A1 | 6/2021 | Prince | |
| 2021/0186467 | A1 | 6/2021 | Urabe et al. | |
| 2021/0201080 | A1* | 7/2021 | Kitahara | G06F 18/2148 |
| 2021/0275256 | A1 | 9/2021 | Sowards et al. | |
| 2021/0315542 | A1 | 10/2021 | Oura et al. | |
| 2021/0322106 | A1 | 10/2021 | Mo et al. | |
| 2022/0013218 | A1 | 1/2022 | Cousin | |
| 2022/0022969 | A1 | 1/2022 | Misener | |
| 2022/0027257 | A1 | 1/2022 | Harutyunyan et al. | |
| 2022/0039685 | A1 | 2/2022 | Misener et al. | |
| 2022/0054869 | A1 | 2/2022 | Stein et al. | |
| 2022/0096797 | A1 | 3/2022 | Prince | |
| 2022/0101980 | A1* | 3/2022 | Rothenberg | G16H 10/60 |
| 2022/0104886 | A1 | 4/2022 | Blanchard et al. | |
| 2022/0117582 | A1 | 4/2022 | McLaughlin et al. | |
| 2022/0142608 | A1 | 5/2022 | Matsumoto | |
| 2022/0160434 | A1 | 5/2022 | Messerly et al. | |
| 2022/0189610 | A1 | 6/2022 | Long et al. | |
| 2022/0230714 | A1 | 7/2022 | Batman et al. | |
| 2022/0241014 | A1 | 8/2022 | Kleyman et al. | |
| 2022/0280246 | A1 | 9/2022 | Messerly et al. | |
| 2022/0304652 | A1 | 9/2022 | Peterson et al. | |
| 2022/0392642 | A1 | 12/2022 | Dasi et al. | |
| 2022/0401157 | A1 | 12/2022 | Sowards et al. | |
| 2022/0406460 | A1* | 12/2022 | Golan | G16H 50/20 |
| 2023/0030941 | A1* | 2/2023 | Han | A61B 8/467 |
| 2023/0121370 | A1 | 4/2023 | Sowards et al. | |
| 2023/0147164 | A1 | 5/2023 | Sowards et al. | |
| 2023/0148993 | A1 | 5/2023 | Sowards et al. | |
| 2023/0225702 | A1* | 7/2023 | Sakalauskas | G16H 50/30 600/454 |
| 2023/0260107 | A1* | 8/2023 | Dhatt | G06N 3/09 382/131 |
| 2023/0329748 | A1 | 10/2023 | Sowards et al. | |
| 2023/0338003 | A1 | 10/2023 | Misener et al. | |
| 2023/0380906 | A1 | 11/2023 | Misener et al. | |
| 2023/0404683 | A1 | 12/2023 | Schmidt et al. | |
| 2023/0420105 | A1 | 12/2023 | Misener et al. | |
| 2024/0156429 | A1 | 5/2024 | Dhatt et al. | |
| 2024/0245386 | A1 | 7/2024 | Prince | |
| 2024/0249831 | A1 | 7/2024 | Jesneck et al. | |
| 2024/0274297 | A1 | 8/2024 | Sillesen et al. | |
| 2024/0390605 | A1 | 11/2024 | Burkholz et al. | |
| 2024/0416077 | A1 | 12/2024 | Andersen et al. | |
| 2025/0000585 | A1 | 1/2025 | Sinha et al. | |
| 2025/0255576 | A1 | 8/2025 | Prince | |

FOREIGN PATENT DOCUMENTS

| | | | |
|---|---|---|---|
| CN | 216167530 | U | 4/2022 |
| EP | 1504713 | A1 | 2/2005 |
| EP | 0788329 | B1 | 12/2006 |
| JP | 2018175547 | A | 11/2018 |
| KR | 20180070878 | A | 6/2018 |
| WO | 2013059714 | A1 | 4/2013 |
| WO | 2014053934 | A1 | 4/2014 |
| WO | 2015/017270 | A1 | 2/2015 |
| WO | 2018/026878 | A1 | 2/2018 |
| WO | 2019/232451 | A1 | 12/2019 |
| WO | 2020/002620 | A1 | 1/2020 |
| WO | 2020150501 | A1 | 7/2020 |
| WO | 2020160550 | A1 | 8/2020 |
| WO | 2020/186198 | A1 | 9/2020 |
| WO | 2021113733 | A1 | 6/2021 |
| WO | 2022/067101 | A1 | 3/2022 |
| WO | 2022/072727 | A2 | 4/2022 |
| WO | 2022/081904 | A1 | 4/2022 |
| WO | 2022150411 | A1 | 7/2022 |
| WO | 2022/187701 | A1 | 9/2022 |
| WO | 2022212414 | A1 | 10/2022 |
| WO | 2022/271728 | A1 | 12/2022 |
| WO | 2022254436 | A1 | 12/2022 |
| WO | 2023064492 | A1 | 4/2023 |
| WO | 2023081414 | A1 | 5/2023 |
| WO | 2023091427 | A1 | 5/2023 |
| WO | 2023205019 | A1 | 10/2023 |
| WO | 2023205052 | A1 | 10/2023 |
| WO | 2023230284 | A1 | 11/2023 |
| WO | 2023244640 | A1 | 12/2023 |
| WO | 2023250001 | A1 | 12/2023 |
| WO | 2024010874 | A1 | 1/2024 |
| WO | 2025064164 | A1 | 3/2025 |

OTHER PUBLICATIONS

PCT/US2023/018680 filed Apr. 14, 2023 International Seach Report and Written Opinion dated Aug. 11, 2013.

PCT/US2023/023616 filed May 25, 2023 International Search Report and Written Opinion dated Aug. 16, 2023.

PCT/US2023/025259 filed Jun. 14, 2023 International Search Report and Written Opinion dated Sep. 25, 2023.

PCT/US2023/025845 filed Jun. 21, 2023 International Search Report and Written Opinion dated Sep. 26, 2023.

PCT/US2023/027042 filed Jul. 6, 2023 International Search Report and Written Opinion dated Oct. 10, 2023.

Schmidt G A et al Ultrasound-guided 1-22 vascular access in critical illness Intensive Care Medicine Springer Berlin Heidelberg Berlin/Heidelberg vol. 45 no. 4 Feb. 18, 2019 Feb. 18, 2019 pp. 434-446 XP036747615 ISSN 0342-4642 DOI 10.1007/S00134-019-05564-7 retrieved on Feb. 181, 2019.

U.S. Appl. No. 17/707,662, filed Mar. 29, 2022 Non-Final Office Action dated Oct. 17, 2023.

Murphy, Ethan K., et al., "Phantom Studies of Fused-Data TREIT Using Only Biopsy-Probe Electrodes" IEEE Transactions on Medical Imaging, IEEE, USA. vol. 39 no. 114, May 2020. (May 4, 2020).

PCT/US2012/061182 International Seach Report and Written Opinion dated Mar. 11, 2013.

PCT/US2020/063441 filed Dec. 4, 2020 International Preliminary Report on Patentability dated May 17, 2022.

PCT/US2020/063441 filed Dec. 4, 2020 International Search Report and Written Opinion dated Mar. 19, 2021.

PCT/US2021/052055 filed Sep. 24, 2021 International Search Report and Written Opinion dated Dec. 20, 2021.

PCT/US2022/019017 filed Mar. 4, 2022 International Search Report and Written Opinion dated Jun. 14, 2022.

PCT/US2022/022400 filed Mar. 29, 2022 International Search Report and Written Opinion dated Jul. 8, 2022.

Sebastian Vogt: "Real-Time Augmented Reality for Image-Guided Interventions", Oct. 5, 2009, XPO55354720, Retrieved from the Internet: URL: https://opus4.kobv.de/opus4-fau/frontdoor/deliver/index/docld/1235/file/SebastianVogtDissertation.pdf.

U.S. Appl. No. 13/656,563, filed Oct. 19, 2012 Decision on Appeal dated Nov. 1, 2017.

U.S. Appl. No. 13/656,563, filed Oct. 19, 2012 Examiner's Answer dated Nov. 16, 2015.

U.S. Appl. No. 13/656,563, filed Oct. 19, 2012 Final Office Action dated Dec. 5, 2014.

U.S. Appl. No. 13/656,563, filed Oct. 19, 2012 Non-Final Office Action dated Jul. 18, 2014.

U.S. Appl. No. 15/951,903, filed Apr. 12, 2018 Advisory Action dated Dec. 22, 2020.

U.S. Appl. No. 15/951,903, filed Apr. 12, 2018 Board Decision dated Apr. 20, 2022.

U.S. Appl. No. 15/951,903, filed Apr. 12, 2018 Examiner's Answer dated Jun. 3, 2021.

U.S. Appl. No. 15/951,903, filed Apr. 12, 2018 Final Office Action dated Oct. 13, 2020.

U.S. Appl. No. 15/951,903, filed Apr. 12, 2018 Non-Final Office Action dated May 22, 2020.

U.S. Appl. No. 15/951,903, filed Apr. 12, 2018 Notice of Allowance dated May 2, 2022.

William F Garrett et al: "Real-time incremental visualization of dynamic ultrasound vols. using parallel BSP trees", Visualization '96. Proceedings, IEEE, NE, Oct. 27, 1996, pp. 235-ff, XPO58399771, ISBN: 978-0-89791-864-0 abstract, figures 1-7, pp. 236-240.

(56) References Cited

OTHER PUBLICATIONS

PCT/US2022/046606 filed Oct. 13, 2022 International Search Report and Written Opinion dated Feb. 6, 2023.
PCT/US2022/049042 filed Nov. 4, 2022 International Search Report and Written Opinion dated Mar. 1, 2023.
PCT/US2022/049989 filed Nov. 15, 2022 International Search Report and Written Opinion dated Feb. 6, 2023.
U.S. Appl. No. 17/112,725, filed Dec. 4, 2020 Final Office Action dated Apr. 14, 2023.
U.S. Appl. No. 17/485,035, filed Sep. 24, 2021 Non-Final Office Action dated May 3, 2023.
U.S. Appl. No. 17/725,370, filed Apr. 20, 2022 Restriction Requirement dated Apr. 27, 2023.
Beigi, P. et al., "Enhancement of needle visualization and localization in ultrasound." International Journal of Computer Assisted Radiology and Surgery, vol. 16, No. 130, Sep. 2020 [Sep. 30, 2020] pp. 169-178.
PCT/US2023/018340 filed Apr. 12, 2023 International Seach Report and Written Opinion dated Jul. 20, 2023.
U.S. Appl. No. 17/725,370, filed Apr. 20, 2022 Non-Final Office Action dated Aug. 4, 2023.
PCT/US2022/034380 filed Jun. 21, 2022 International Search Report and Written Opinion dated Oct. 5, 2022.
U.S. Appl. No. 17/112,735, filed Dec. 4, 2022 Non-Final Office Action dated Oct. 26, 2022.
U.S. Appl. No. 17/485,035, filed Sep. 24, 2021 Notice of Allowance dated Nov. 8, 2023.
U.S. Appl. No. 17/707,662, filed Mar. 29, 2022 Advisory Action dated Feb. 23, 2024.
U.S. Appl. No. 17/707,662, filed Mar. 29, 2022 Final Office Action dated Apr. 22, 2024.
U.S. Appl. No. 17/707,662, filed Mar. 29, 2022 Final Office Action dated Dec. 20, 2023.
U.S. Appl. No. 17/724,371, filed Apr. 19, 2022 Non-Final Office Action dated Apr. 12, 2024.
U.S. Appl. No. 17/725,370, filed Apr. 20, 2022 Final Office Action dated Feb. 15, 2024.
U.S. Appl. No. 17/825,976, filed May 26, 2022 Restriction Requirement dated Apr. 12, 2024.
U.S. Appl. No. 17/724,371, filed Apr. 19, 2022 Final Office Action dated Jul. 24, 2024.
U.S. Appl. No. 17/849,455, filed Jun. 24, 2022 Non-Final Office Action dated Jul. 18, 2024.
U.S. Appl. No. 17/687,476, filed Mar. 4, 2022 Non-Final Office Action dated Nov. 1, 2024.
U.S. Appl. No. 17/707,662, filed Mar. 29, 2022 Examiner's Answer dated Oct. 23, 2024.
U.S. Appl. No. 17/724,371, filed Apr. 19, 2022 Advisory Action dated Sep. 20, 2024.
U.S. Appl. No. 17/724,371, filed Apr. 19, 2022 Non-Final Office Action dated Nov. 26, 2024.
U.S. Appl. No. 17/725,370, filed Apr. 20, 2022 Notice of Allowance dated Sep. 18, 2024.
U.S. Appl. No. 17/825,976, filed May 26, 2022 Non-Final Office Action dated Oct. 4, 2024.
U.S. Appl. No. 17/849,455, filed Jun. 24, 2022 Final Office Action dated Nov. 7, 2024.
U.S. Appl. No. 17/981,313, filed Nov. 4, 2022 Non-Final Office Action dated Oct. 8, 2024.
U.S. Appl. No. 18/601,980, filed Mar. 11, 2024 Non-Final Office Action dated Sep. 27, 2024.
PCT/US2023/025845 filed Jun. 21, 2023 International Preliminary Report on Patentability dated Dec. 18, 2024.
U.S. Appl. No. 17/845,818, filed Jun. 21, 2022 Restriction Requirement dated Feb. 10, 2025.
U.S. Appl. No. 17/849,455, filed Jun. 24, 2022 Advisory Action dated Dec. 17, 2024.
U.S. Appl. No. 17/849,455, filed Jun. 24, 2022 Non-Final Office Action dated Jan. 24, 2025.
U.S. Appl. No. 17/965,657, filed Oct. 13, 2022 Non-Final Office Action dated Jan. 6, 2025.
U.S. Appl. No. 18/601,980, filed Mar. 11, 2024 Notice of Allowance dated Jan. 10, 2025.
U.S. Appl. No. 17/687,476, filed Mar. 4, 2022 Notice of Allowance dated Mar. 5, 2025.
U.S. Appl. No. 17/724,371, filed Apr. 19, 2022 Advisory Action dated May 14, 2025.
U.S. Appl. No. 17/724,371, filed Apr. 19, 2022 Final Office Action dated Mar. 7, 2025.
U.S. Appl. No. 17/724,371, filed Apr. 19, 2022 Non-Final Office Action dated Jun. 12, 2025.
U.S. Appl. No. 17/825,976, filed May 26, 2022 Advisory Action dated Jun. 9, 2025.
U.S. Appl. No. 17/825,976, filed May 26, 2022 Final Office Action dated Mar. 25, 2025.
U.S. Appl. No. 17/825,976, filed May 26, 2022 Non-Final Office Action dated Aug. 5, 2025.
U.S. Appl. No. 17/841,541, filed Jun. 15, 2022 Final Office Action dated Jul. 23, 2025.
U.S. Appl. No. 17/841,541, filed Jun. 15, 2022 Non-Final Office Action dated Mar. 14, 2025.
U.S. Appl. No. 17/845,818, filed Jun. 21, 2022 Non-Final Office Action dated Jun. 17, 2025.
U.S. Appl. No. 17/849,455, filed Jun. 24, 2022 Advisory Action dated Jul. 11, 2025.
U.S. Appl. No. 17/849,455, filed Jun. 24, 2022 Final Office Action dated May 7, 2025.
U.S. Appl. No. 17/849,455, filed Jun. 24, 2022 Non-Final Office Action dated Sep. 5, 2025.
U.S. Appl. No. 17/965,657, filed Oct. 13, 2022 Final Office Action dated May 22, 2025.
U.S. Appl. No. 17/981,313, filed Nov. 4, 2022 Advisory Action dated Jun. 26, 2025.
U.S. Appl. No. 17/981,313, filed Nov. 4, 2022 Final Office Action dated Apr. 15, 2025.
U.S. Appl. No. 17/981,313, filed Nov. 4, 2022 Non-Final Office Action dated Jul. 22, 2025.
U.S. Appl. No. 17/987,717, filed Nov. 15, 2022 Non-Final Office Action dated Mar. 21, 2025.
U.S. Appl. No. 17/987,717, filed Nov. 15, 2022 Notice of Allowance dated Jul. 15, 2025.
U.S. Appl. No. 17/707,662, filed Mar. 29, 2022 Board Decision dated Nov. 26, 2025.
U.S. Appl. No. 17/724,371, filed Apr. 19, 2022 Final Office Action dated Oct. 29, 2025.
U.S. Appl. No. 17/841,541, filed Jun. 15, 2022 Non-Final Office Action dated Dec. 1, 2025.
U.S. Appl. No. 17/845,818, filed Jun. 21, 2022 Notice of Allowance dated Oct. 28, 2025.
U.S. Appl. No. 17/965,657, filed Oct. 13, 2022 Notice of Allowance dated Sep. 24, 2025.
U.S. Appl. No. 17/707,662, filed Mar. 29, 2022 Notice of Allowance dated Dec. 23, 2025.
U.S. Appl. No. 17/724,371, filed Apr. 19, 2022 Advisory Action dated Jan. 9, 2026.
U.S. Appl. No. 17/825,976, filed May 26, 2022 Final Office Action dated Feb. 5, 2026.
U.S. Appl. No. 17/849,455, filed Jun. 24, 2022 Advisory Action dated Mar. 9, 2026.
U.S. Appl. No. 17/849,455, filed Jun. 24, 2022 Final Office Action dated Dec. 29, 2025.
U.S. Appl. No. 17/981,313, filed Nov. 4, 2022 Final Office Action dated Jan. 27, 2026.
U.S. Appl. No. 17/724,371, filed Apr. 19, 2022 Examiner's Answer dated Apr. 27, 2026.
U.S. Appl. No. 17/825,976, filed May 26, 2022 Advisory Action dated Apr. 9, 2026.
U.S. Appl. No. 17/841,541, filed Jun. 15, 2022 Final Office Action dated Apr. 20, 2026.

(56) References Cited

OTHER PUBLICATIONS

U.S. Appl. No. 17/849,455, filed Jun. 24, 2022 Non-Final Office Action dated May 21, 2026.

* cited by examiner

SYSTEMS AND METHODS FOR AUTOMATIC DETERMINATION OF NEEDLE GUIDES FOR VASCULAR ACCESS

BACKGROUND

Currently, clinicians determine which needle guides to use for establishing vascular access via needles when preparing therefor by way of ultrasound imaging; however, clinician-selected needle guides are not always the best needle guides for establishing vascular access in view of multifaceted considerations of applicable criteria.

Disclosed herein are systems and methods for automatically determining needle guides to use for establishing vascular access.

SUMMARY

Disclosed herein is a system for automatic determination of a needle guide for establishing vascular access. The system includes, in some embodiments, an ultrasound probe, a console operably coupled to the ultrasound probe, and a display screen optionally integrated into the console. The console includes one or more processors and memory including instructions configured to instantiate one or more processes when executed by the one-or-more processors for the automatic determination of the needle guide in accordance with ultrasound-imaging data, historical data, or a combination thereof. The automatic determination of the needle guide uses at least logic, algorithms, machine learning including a machine-learning model trained with the historical data, artificial intelligence, or a combination thereof. The display screen is configured to display an ultrasound image including one or more blood vessels below a skin surface of a patient as well as the needle guide resulting from the automatic determination of the needle guide for establishing vascular access to the one-or-more blood vessels in the ultrasound image.

In some embodiments, the system is further configured for automatic selection of a blood vessel of the one-or-more blood vessels for establishing vascular access in accordance with the ultrasound-imaging data, the historical data, or a combination thereof. The automatic selection of the blood vessel uses at least the logic, the algorithms, the machine learning, the artificial intelligence, or a combination thereof.

In some embodiments, the machine learning, the artificial intelligence, or both perform image recognition using the ultrasound-imaging data for the automatic selection of the blood vessel.

In some embodiments, the automatic selection of the blood vessel is optimized within an image buffer or window via one or more blood vessel-selection algorithms.

In some embodiments, the machine learning, the artificial intelligence, or both analyze Doppler ultrasound-imaging data when available for the automatic selection of the blood vessel.

In some embodiments, the automatic determination of the needle guide is further in accordance with a location of the blood vessel resulting from the automatic selection of the blood vessel.

In some embodiments, the needle guide resulting from the automatic determination of the needle guide is further in accordance with blood-vessel size of the blood vessel resulting from the automatic selection of the blood vessel.

In some embodiments, the needle guide resulting from the automatic determination of the needle guide is from a group of possible needle guides that vary by angle of approach, depth at image intersection, compatible needle sizes, or a combination thereof.

In some embodiments, the needle guide resulting from the automatic determination of the needle guide is further in accordance with trigonometric calculations resulting from a trigonometric algorithm of the algorithms.

In some embodiments, the system is further configured for automatic determination of a vascular access device ("VAD") from an inventory of available VADs in accordance with the ultrasound-imaging data. The automatic determination of the VAD using at least the logic, the algorithms, the machine learning, the artificial intelligence, or a combination thereof is in view of VAD occupancy of the blood vessel or VAD purchase length of the blood vessel for each VAD of the inventory of available VADs.

In some embodiments, the historical data includes clinician feedback entered into the condole on whether the needle guide resulting from the automatic determination of the needle guide was successful in establishing vascular access.

Also disclosed herein is a method of a system for automatic determination of a needle guide for establishing vascular access. The method includes, in some embodiments, an instantiating step, a needle-guide determining step, and a displaying step. The instantiating step includes instantiating one or more processes by executing instructions therefor stored in memory of a console of the system by one or more processors of the console. The needle-guide determining step includes automatically determining the needle guide in accordance with ultrasound-imaging data gathered by an ultrasound probe operably coupled to the console, historical data, or a combination thereof. The needle-guide determining step uses at least logic, algorithms, machine learning including a machine-learning model trained with the historical data, artificial intelligence, or a combination thereof. The displaying step includes displaying on a display screen optionally integrated into the console an ultrasound image including one or more blood vessels below a skin surface of a patient. The displaying step also includes displaying the needle guide resulting from needle-guide determining step for establishing vascular access to the one-or-more blood vessels in the ultrasound image.

In some embodiments, the method further includes a blood vessel-selecting step. The blood vessel-selecting step includes automatically selecting a blood vessel of the one-or-more blood vessels for establishing vascular access in accordance with the ultrasound-imaging data, the historical data, or a combination thereof. The blood vessel-selecting step uses at least the logic, the algorithms, the machine learning, the artificial intelligence, or a combination thereof.

In some embodiments, the method further includes an image-recognizing step. The image-recognizing step includes performing image recognition with the machine learning, the artificial intelligence, or both using the ultrasound-imaging data for the blood vessel-selecting step.

In some embodiments, the method further includes a blood-vessel selection-optimizing step. The blood-vessel selection-optimizing step includes optimizing the automatic selection of the blood vessel within an image buffer or window via one or more blood vessel-selection algorithms.

In some embodiments, the method further includes a Doppler-analyzing step. The Doppler-analyzing step includes analyzing Doppler ultrasound-imaging data with the machine learning, the artificial intelligence, or both in the blood vessel-selecting step.

In some embodiments, the needle-guide determining step is further in accordance with a location of the blood vessel resulting from the blood vessel-selecting step.

In some embodiments, the needle guide resulting from the needle-guide determining step is further in accordance with blood-vessel size of the blood vessel resulting from the blood vessel-selecting step.

In some embodiments, the needle guide resulting from the needle-guide determining step is from a group of possible needle guides that vary by angle of approach, depth at image intersection, compatible needle sizes, or a combination thereof.

In some embodiments, the needle guide resulting from the needle-guide determining step is further in accordance with trigonometric calculations resulting from a trigonometric algorithm of the algorithms.

In some embodiments, the method further includes a VAD-determining step. The VAD-determining step includes automatically determining a VAD from an inventory of available VADs in accordance with the ultrasound-imaging data, the automatic determination of the VAD using at least the logic, the algorithms, the machine learning, the artificial intelligence, or a combination thereof in view of VAD occupancy of the blood vessel or VAD purchase length of the blood vessel for each VAD of the inventory of available VADs.

In some embodiments, the historical data includes clinician feedback entered into the condole on whether the needle guide resulting from the needle guide-determining step was successful in establishing vascular access.

These and other features of the concepts provided herein will become more apparent to those of skill in the art in view of the accompanying drawings and following description, which describe particular embodiments of such concepts in greater detail.

DRAWINGS

DESCRIPTION

Figure 1:
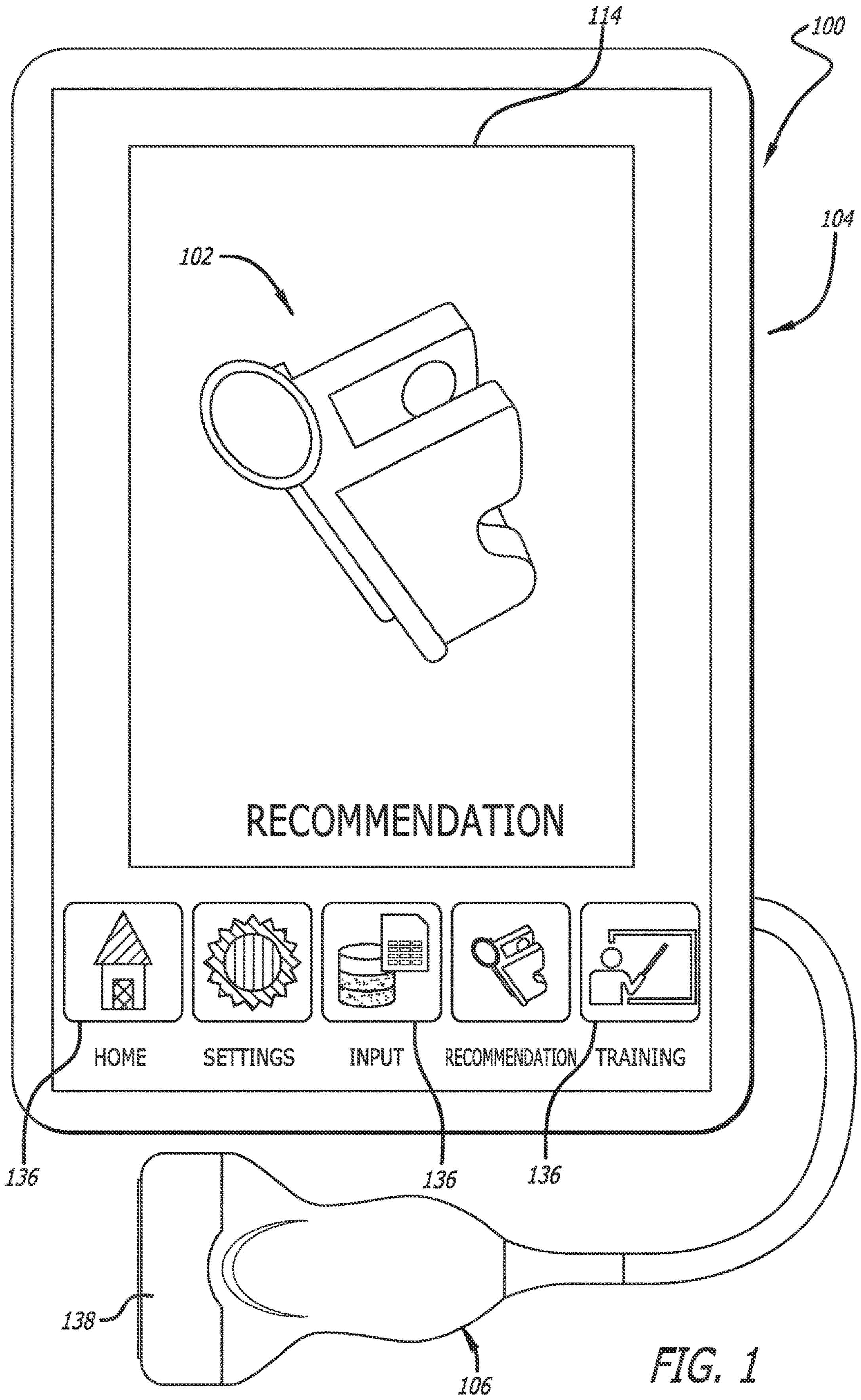
FIG. 1 illustrates a system for automatic determination of a needle guide for establishing vascular access in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. In addition, any of the foregoing features or steps can, in turn, further include one or more features or steps unless indicated otherwise. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "logic," logic refers to hardware, software, or firmware configured to perform one or more functions. As hardware, logic can refer to circuitry having data-processing or storage functionality. Examples of such circuitry include, but are not limited to, a hardware processor (e.g., a microprocessor, one or more processor cores, a digital-signal processor, a programmable gate array ["PGA"], a microcontroller, an application specific integrated circuit ["ASIC"], etc.), semiconductor memory, or the like. As software, logic can refer to one or more processes, one or more instances, Application Programming Interface (s) (API), subroutine(s), function(s), applet(s), servlet(s), routine(s), source code, object code, shared or dynamic link libraries (dll), or even one or more instructions. Such software can be stored in any type of a suitable non-transitory storage medium or transitory storage medium (e.g., electrical signals, optical signals, acoustical signals, or some other form of propagated signals). Examples of a non-transitory storage medium include, but are not limited to, a programmable circuit; a non-persistent storage medium such as volatile memory (e.g., any type of random-access memory ["RAM"]); a persistent storage medium such as non-volatile memory (e.g., read-only memory ["ROM"], power-backed RAM, flash memory, phase-change memory, etc.), a solid-state drive, a hard-disk drive, an optical-disc drive, or a portable memory device. As firmware, logic can be stored in persistent storage.

As used herein, a "vascular access device" can be a medical device for vascular access including, but not limited to, a catheter such as a peripherally inserted central catheter ("PICC"), a central venous catheter ("CVC"), a midline catheter, an intravenous line such as a peripheral intravenous line ("Ply"), or the like.

Unless defined otherwise, all technical and scientific terms used herein have the same meaning as commonly understood by those of ordinary skill in the art.

Again, clinicians currently determine which needle guides to use for establishing vascular access via needles when preparing therefor by way of ultrasound imaging; however, clinician-selected needle guides are not always the best needle guides for establishing vascular access in view of multifaceted considerations of applicable criteria.

Disclosed herein are systems and methods for automatically determining needle guides to use for establishing vascular access.

Systems

Figure 2:
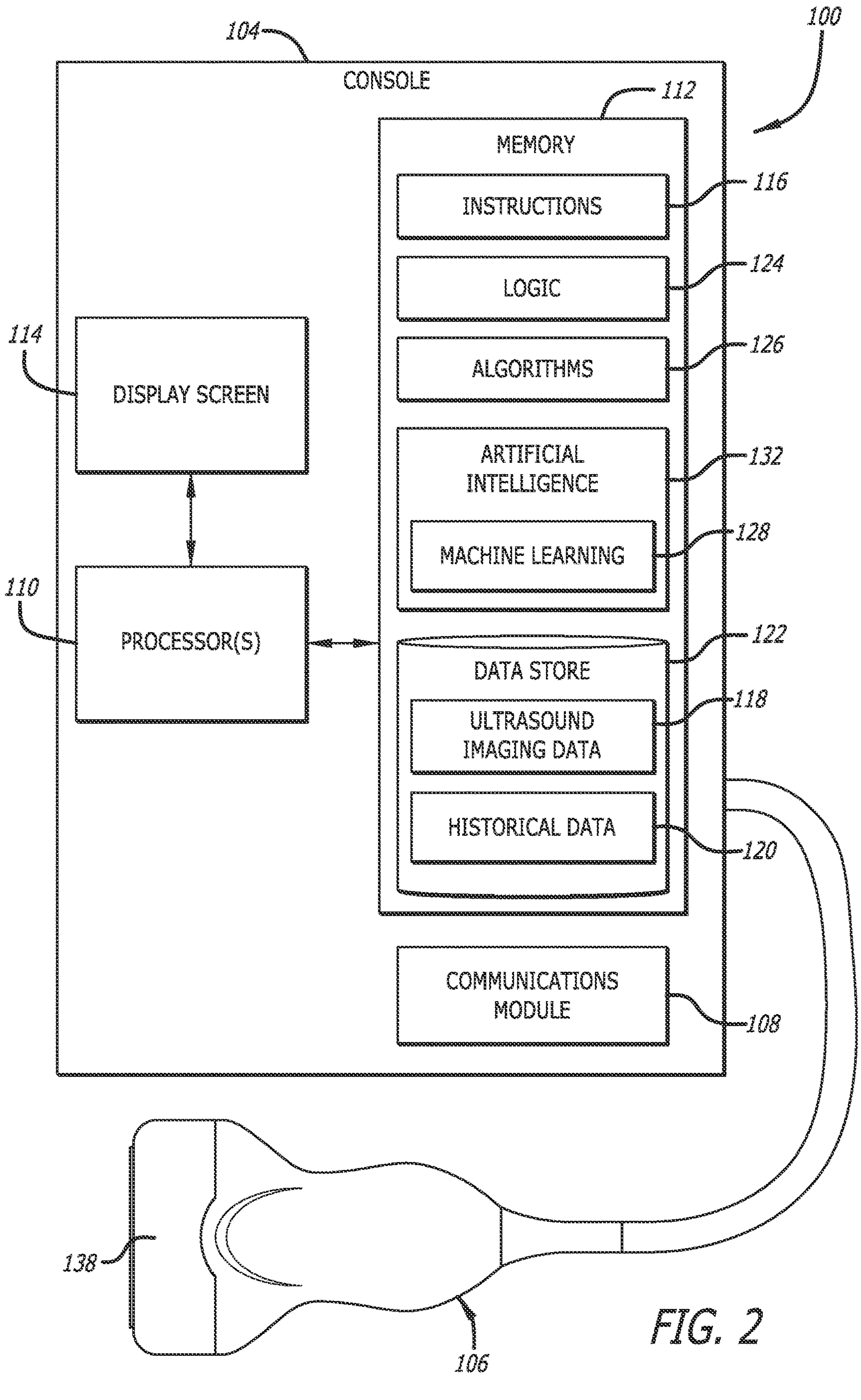
FIG. 2 illustrates a block diagram of the system of FIG. 1 in accordance with some embodiments.

FIG. 1 illustrates a system 100 for automatic determination of a needle guide 102 for establishing vascular access in accordance with some embodiments. FIG. 2 illustrates a block diagram of the system 100 of FIG. 1 in accordance with some embodiments.

As shown, the system 100 can include a console 104 and an ultrasound probe 106 configured to operably couple with each other. For example, the console 104 and the ultrasound probe 106 can be coupled together via wire or wirelessly through communications modules such as the communications module 108 of the console 104 shown in FIG. 2.

The console 104 can include one or more processors 110 and memory 112. Optionally, the console 104 can further include a display screen 114 (e.g., touch screen).

The memory 112 can include random-access memory ("RAM") or non-volatile memory (e.g., electrically erasable programmable read-only memory ["EEPROM"]), and the one-or-more processors 110 and the memory 112 of the console 104 can be configured to control various functions of the system 100, as well as executing various operations (e.g., processing electrical signals from the ultrasonic transducers of the ultrasound probe 106 into ultrasound images) during operation of the system 100 in accordance with executable instructions 116 therefor stored in the memory 112 for execution by the one-or-more processors 110. Indeed, the instructions 116 can be configured to instantiate one or more processes when executed by the one-or-more processors 110 for the automatic determination of the needle guide 102 in accordance with ultrasound-imaging data 118, historical data 120, or a combination thereof stored, at least temporarily (e.g., prior to a procedure), in a data store 122. However, the one-or-more processes are not limited to automatic determinations of needle guides. In an example, the one-or-more processes can also include automatic selection of a blood vessel of one or more blood vessels for establishing vascular access in accordance with the ultrasound-imaging data 118, the historical data 120, or a combination thereof. In another example, the one-or-more processes can also include automatic determination of a VAD from an inventory of available VADs in accordance with at least the ultrasound-imaging data 118, particularly in view of VAD occupancy of the blood vessel or VAD purchase length of the blood vessel for each VAD of the inventory of available VADs. Such automatic determinations can use at least logic 124, algorithms 126, machine learning 128 including one or more machine-learning models ("MLMs") 130 trained with the historical data 120 for continuously improving needle-guide determinations, artificial intelligence 132 (e.g., an artificial neural network ["ANN"]), or a combination thereof.

As to the automatic selection of the blood vessel of the one-or-more blood vessels for establishing vascular access, the automatic selection of the blood vessel can be, again, in accordance with the ultrasound-imaging data 118, the historical data 120, or a combination thereof. Indeed, the machine learning 128, the artificial intelligence 132, or both can perform image recognition using at least the ultrasound-imaging data 118 for the automatic selection of the blood vessel, which can include a determination of blood-vessel size and location including depth of the blood vessel (see FIG. 4) for subsequent automatic determination of the needle guide 102. Notably, the automatic selection of the blood vessel can be optimized within an image buffer or window via one or more blood vessel-selection algorithms of the algorithms 126. (See, for example, US 2022/0117582, which is incorporated herein in its entirety.) In addition, the machine learning 128, the artificial intelligence 132, or both can analyze Doppler ultrasound-imaging data (e.g., a subset of the ultrasound-imaging data 118) when available for the automatic selection of the blood vessel in view of blood flow characteristics. Notwithstanding the foregoing, user selection can override automatic selection of the blood vessel or any other automatically selected target for that matter.

As to the automatic determination of the needle guide 102 for establishing vascular access, the automatic determination of the needle guide 102 can be, again, in accordance with the ultrasound-imaging data 118, the historical data 120, or a combination thereof. Indeed, the machine learning 128, the artificial intelligence 132, or both can automatically determine the needle guide 102 in accordance with the blood-vessel size of the blood vessel resulting from the automatic selection of the blood vessel, location of the blood vessel resulting from the automatic selection of the blood vessel, which can include trigonometric calculations resulting from a trigonometric algorithm of the algorithms 126. Notably, the needle guide 102 resulting from the automatic determination of the needle guide 102 can be from a group of possible needle guides that vary by angle of approach, depth at image intersection, compatible needle sizes, or a combination thereof.

Figure 3:
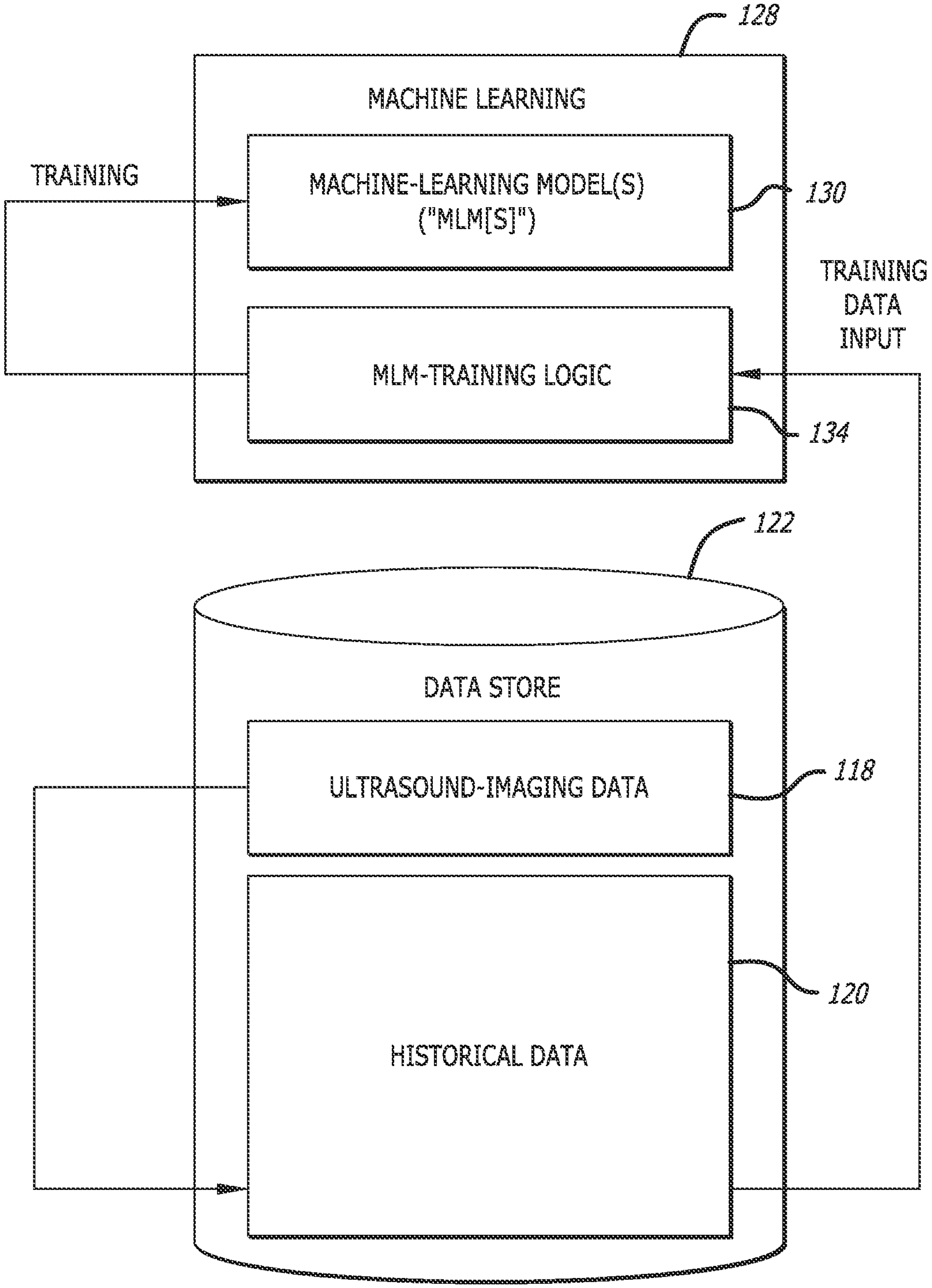
FIG. 3 illustrates training one or more machine-learning models ("MLMs") with historical data of the system in accordance with some embodiments.

FIG. 3 illustrates training the one-or-more MLMs 130 with the historical data 120 of the system 100 in accordance with some embodiments.

The machine learning 128 can include the one-or-more MLMs 130 and MLM-training logic 134 as shown in FIG. 3. The MLM-training logic 134 can be configured to provide the one-or-more MLMs 130 with the historical data 120 as training data when training the one-or-more MLMs 130 to learn from the training data in accordance with supervised learning, semi-supervised learning, or unsupervised learning. Notably, the historical data 120 can include the ultrasound-imaging data 118 and any procedural data from previous procedures automatically pulled into the system 100 or manually input into the system 100 by a clinician using the system 100. For example, the historical data 120 can include clinician feedback entered into the console 104 on whether the needle guide 102 resulting from the automatic determination of the needle guide 102 was successful in establishing vascular access for system-determined blood vessel of a known blood-vessel size and location. Such historical data 120 can also be labeled by the MLM-training logic 134 as appropriate for the supervised or semi-supervised training.

The display screen 114 can be integrated into the console 104, as shown, or the display screen 114 can be part of a standalone monitor configured to operably couple with the console 104. The display screen 114 can be configured to display an ultrasound image including one or more blood vessels below a skin surface of a patient, for example, as alluded to in FIG. 4. The display screen 114 can also be configured to display, for example, a picture or drawing of the needle guide 102, a written description of the needle guide 102, or both resulting from the automatic determination of the needle guide 102 for establishing vascular access to the one-or-more blood vessels in the ultrasound image. Notably, the display screen 114 can also be configured to display one or more on-screen buttons 136 (e.g., a home button, a settings button, a data-input button, a needle-guide recommendation button, a training button, etc.) enabling the clinician to interact with various aspects of the system 100. For example, the one-or-more on-screen buttons 136 can include the example needle-guide recommendation button, which the clinician can press when any preassessment of the patient is complete. (See FIG. 4, which, in part, depicts preassessment of the patient and a vessel V at a depth d. and a picture of the needle guide 102 resulting from the automatic determination of the needle guide 102 for establishing vascular access to the vessel V.)

While not shown, the console 104 can further include a power connection configured to enable an operable connection to an external power supply. An internal power supply (e.g., a battery) can also be employed either with or exclusive of the external power supply. Power management circuitry of the console 104 can regulate power use and distribution.

Figure 4:
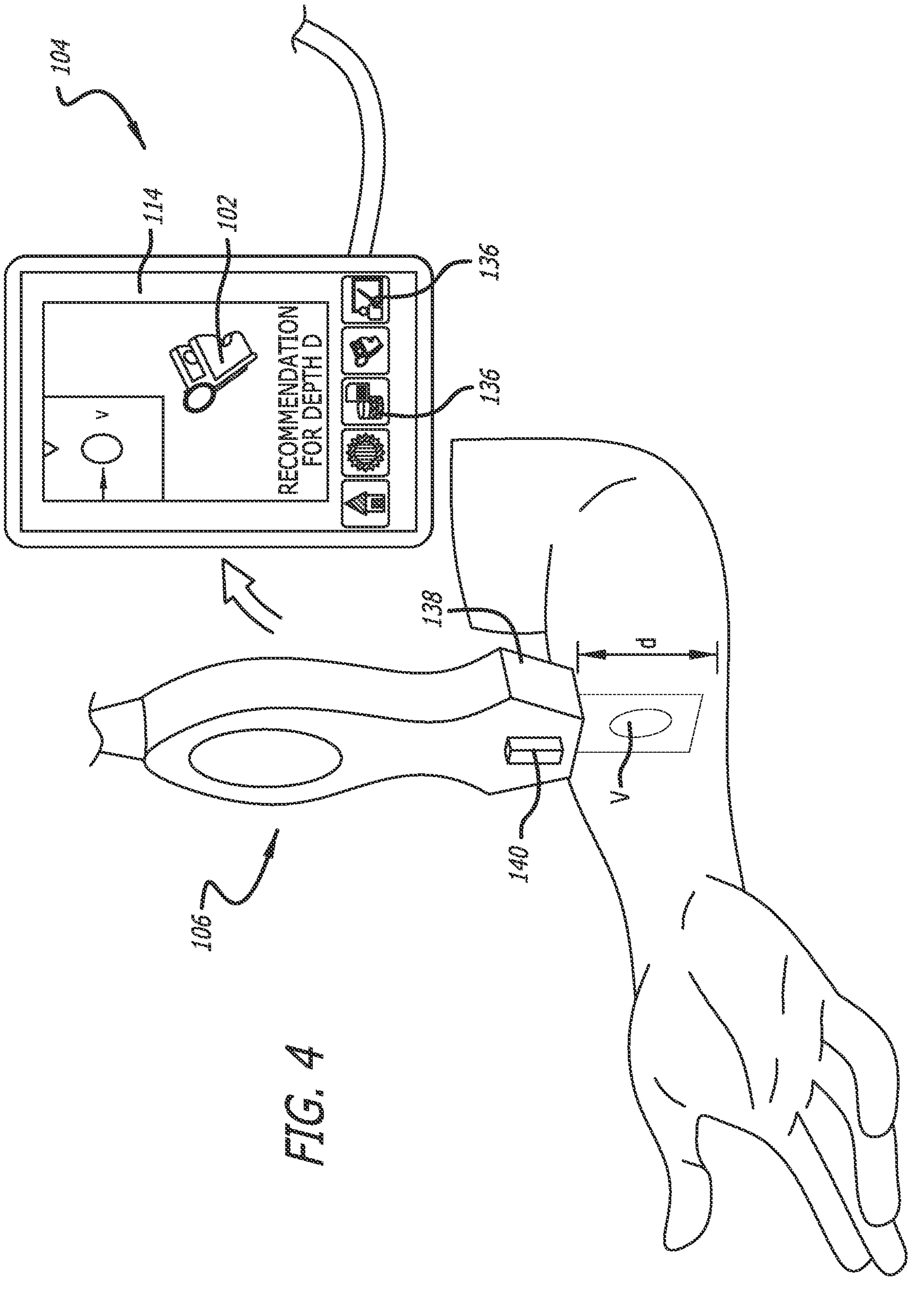
FIG. 4 illustrates a method for automatic determination of a needle guide for establishing vascular access in accordance with some embodiments.

The ultrasound probe 106 can include a probe head 138 housing an array of ultrasonic transducers, wherein the ultrasonic transducers are piezoelectric ultrasonic transducers or capacitive micromachined ultrasonic transducers ("CMUTs"). As shown in FIG. 4, the probe head 138 can be configured for placement against the skin surface of the patient proximate a prospective site for placing the medical device for vascular access, where the ultrasonic transducers in the probe head 138 can generate ultrasound signals and emit the generated ultrasound signals into the patient in a number of pulses, receive reflected ultrasound signals or ultrasound echoes from the patient by way of reflection of the generated ultrasonic pulses by the body of the patient, and convert the reflected ultrasound signals into corresponding electrical signals for processing into the ultrasound image by the console 104. Notably, the ultrasound probe 106 or the probe head 138 thereof can include a needle-guide attachment point 140 for attaching the needle guide 102 automatically determined by the system 100 for establishing vascular access.

Methods

FIG. 4 illustrates a portion of a method of the system 100 for automatic determination of the needle guide 102 for establishing vascular access in accordance with some embodiments.

Methods can include at least the portion of the method of the system 100 shown in FIG. 4 for the automatic determination of the needle guide 102 for establishing vascular access. Indeed, such a method can include one or more steps selected from an instantiating step, a blood vessel-selecting step, an image-recognizing step, a Doppler-analyzing step, a blood-vessel selection-optimizing step, a needle-guide determining step, a VAD-determining step, and a displaying step.

The instantiating step can include instantiating the one-or-more processes set forth above by executing the instructions 116 therefor stored in the memory 112 of the console 104 of the system 100 by the one-or-more processors 110 of the console 104.

The blood vessel-selecting step can include automatically selecting a blood vessel of one or more blood vessels for establishing vascular access in accordance with the ultrasound-imaging data 118, the historical data 120, or a combination thereof. As set forth above, the blood vessel-selecting step can use at least the logic 124, the algorithms 126, the machine learning 128, the artificial intelligence 132, or a combination thereof.

The image-recognizing step can include performing image recognition with the machine learning 128, the artificial intelligence 132, or both using the ultrasound-imaging data 118 for blood vessel-selecting step.

The Doppler-analyzing step can include analyzing Doppler ultrasound-imaging data (e.g., a subset of the ultrasound-imaging data 118) with the machine learning 128, the artificial intelligence 132, or both in the blood vessel-selecting step.

The blood-vessel selection-optimizing step can include optimizing the automatic selection of the blood vessel within an image buffer or window via one or more blood vessel-selection algorithms of the algorithms 126.

The needle-guide determining step can include automatically determining the needle guide 102 in accordance with the ultrasound-imaging data 118 gathered by the ultrasound probe 106 operably coupled to the console 104, the historical data 120, or a combination thereof, which, notably, can include blood-vessel size and location including depth of the blood vessel from the blood vessel-selecting step. As set forth above, the needle-guide determining step can use at least the logic 124, the algorithms 126, the machine learning 128, the artificial intelligence 132, or a combination thereof. The needle guide 102 resulting from the needle-guide determining step can be from a group of possible needle guides that vary by angle of approach, depth at image intersection, compatible needle sizes, or a combination thereof.

The VAD-determining step can include automatically determining a VAD from an inventory of available VADs in accordance with the ultrasound-imaging data 118, the automatic determination of the VAD using at least the logic 124, the algorithms 126, the machine learning 128, the artificial intelligence 132, or a combination thereof in view of VAD occupancy of the blood vessel or VAD purchase length of the blood vessel for each VAD of the inventory of available VADs.

The displaying step can include displaying on the display screen 114 optionally integrated into the console 104 an ultrasound image including the one-or-more blood vessels below a skin surface of a patient. The displaying step can also include displaying the needle guide 102 resulting from the needle-guide determining step for establishing vascular access to the one-or-more blood vessels in the ultrasound image. Such displaying on the display screen 114 is illustrated in FIG. 4.

While some particular embodiments have been disclosed herein, and while the particular embodiments have been disclosed in some detail, it is not the intention for the particular embodiments to limit the scope of the concepts provided herein. Additional adaptations or modifications can appear to those of ordinary skill in the art, and, in broader aspects, these adaptations or modifications are encompassed as well. Accordingly, departures may be made from the particular embodiments disclosed herein without departing from the scope of the concepts provided herein.

What is claimed is:

1. A system configured for automatic determination of a needle guide for establishing vascular access, comprising:

an ultrasound probe;

a console operably coupled to the ultrasound probe, the console including:

one or more processors;

a memory including instructions configured to instantiate one or more processes when executed by the one or more processors for:

the automatic determination of the needle guide in accordance with ultrasound-imaging data and historical data including data from previous procedures regarding whether a previous needle guide was successful for establishing vascular access in a patient, the automatic determination of the needle guide using at least a machine-learning model trained with the historical data;

automatic selection of a blood vessel of one or more blood vessels below a skin surface of the patient for establishing vascular access in accordance with the ultrasound-imaging data and the historical data, the automatic selection of the blood vessel using at least the machine-learning model trained with the historical data; and automatic determination of a vascular access device ("VAD") from an inventory of available VADs in accordance with the ultrasound-imaging data, the automatic determination of the VAD using at least the machine-learning model trained with the historical data in view of VAD occupancy of the blood vessel or VAD purchase length of the blood vessel for each VAD of the inventory of available VADs; and a display screen optionally integrated into the console, the display screen configured to display: an ultrasound image including the one or more blood vessels below the skin surface of the patient; and the needle guide resulting from the automatic determination of the needle guide for establishing vascular access to the one or more blood vessels in the ultrasound image.

2. The system of claim 1, wherein the machine-learning model trained with the historical data performs image recognition using the ultrasound-imaging data for the automatic selection of the blood vessel.

3. The system of claim 2, wherein the automatic selection of the blood vessel is optimized within an image buffer or a window via one or more blood vessel-selection algorithms.

4. The system of claim 1, wherein the machine-learning model trained with the historical data analyzes Doppler ultrasound-imaging data when available for the automatic selection of the blood vessel.

5. The system of claim 1, wherein the automatic determination of the needle guide is further in accordance with a location of the blood vessel resulting from the automatic selection of the blood vessel.

6. The system of claim 1, wherein the needle guide resulting from the automatic determination of the needle guide is further in accordance with blood-vessel size of the blood vessel resulting from the automatic selection of the blood vessel.

7. The system of claim 1, wherein the needle guide resulting from the automatic determination of the needle guide is from a group of possible needle guides that vary by angle of approach, depth at image intersection, compatible needle sizes, or a combination thereof.

8. The system of claim 7, wherein the needle guide resulting from the automatic determination of the needle guide is further in accordance with trigonometric calculations resulting from a trigonometric algorithm of one or more blood vessel-selection algorithms.

9. The system of claim 1, wherein the historical data includes clinician feedback entered into the console on whether the needle guide resulting from the automatic determination of the needle guide was successful in establishing vascular access.

10. The system of claim 1, wherein the machine-learning model is trained to learn from the historical data in accordance with supervised learning.

11. The system of claim 1, wherein the machine-learning model is trained to learn from the historical data in accordance with semi-supervised learning.

12. The system of claim 1, wherein the machine-learning model is trained to learn from the historical data in accordance with unsupervised learning.

13. A method of a system for automatic determination of a needle guide for establishing vascular access, comprising:

instantiating one or more processes by executing instructions therefor stored in memory of a console of the system by one or more processors of the console;

automatically determining of the needle guide in accordance with ultrasound-imaging data gathered by an ultrasound probe operably coupled to the console and historical data including data from previous procedures regarding whether a previous needle guide was successful for establishing vascular access in a patient, the automatic determining of the needle guide using at least a machine-learning model trained with the historical data;

automatically selecting a blood vessel of one-or-more blood vessels below a skin surface of the patient for establishing vascular access in accordance with the ultrasound-imaging data and the historical data, the automatic selecting of the blood vessel using at least the machine-learning model trained with the historical data;

automatically determining a vascular access device ("VAD") from an inventory of available VADs in accordance with the ultrasound-imaging data, the automatic determination of the VAD using at least the machine-learning model trained with the historical data in view of VAD occupancy of the blood vessel or VAD purchase length of the blood vessel for each VAD of the inventory of available VADs; and displaying on a display screen optionally integrated into the console an ultrasound image including the one or more blood vessels below the skin surface of the patient and the needle guide resulting from the automatic determination of the needle guide for establishing vascular access to the one-or-more blood vessels in the ultrasound image.

14. The method of claim 13, further comprising: performing image recognition with the machine learning model trained with the historical data using the ultrasound-imaging data for the automatic selection of the blood vessel.

15. The method of claim 14, further comprising: optimizing the automatic selection of the blood vessel within an image buffer or window via one or more blood vessel-selection algorithms.

16. The method of claim 13, further comprising: analyzing Doppler ultrasound-imaging data with the machine learning model trained with the historical data for the automatic selection of the blood vessel.

17. The method of claim 13, wherein the automatic determination of the needle guide is further in accordance with a location of the blood vessel resulting from the automatic selection of the blood vessel.

18. The method of claim 13, wherein the needle guide resulting from the automatic determination of the needle guide is further in accordance with blood-vessel size of the blood vessel resulting from the automatic selection of the blood vessel.

19. The method of claim 13, wherein the needle guide resulting from the automatic determination of the needle guide is from a group of possible needle guides that vary by angle of approach, depth at image intersection, compatible needle sizes, or a combination thereof.

20. The method of claim 19, wherein the needle guide resulting from the automatic determination of the needle guide is further in accordance with trigonometric calculations resulting from a trigonometric algorithm of one or more blood vessel selection algorithms.

21. The method of claim 13, wherein the historical data includes clinician feedback entered into the console on whether the needle guide resulting from the automatic determination of the needle guide was successful in establishing vascular access.

* * * * *